United States Patent [19]

Laue et al.

[11] Patent Number: 4,994,161

[45] Date of Patent: Feb. 19, 1991

[54] APPARATUS AND METHOD FOR MACROMOLECULAR CHARGE DETERMINATION

[75] Inventors: Thomas M. Laue, Durham, N.H.; David A. Yphantis, Mansfield Center, Conn.; Andrea L. Hazard, Rochester, N.Y.

[73] Assignee: University of New Hampshire, Durham, N.H.

[21] Appl. No.: 305,107

[22] Filed: Feb. 2, 1989

[51] Int. Cl.[5] .................... G01N 27/26; G01N 27/28
[52] U.S. Cl. .............................. 204/180.1; 204/301; 204/182.3; 204/182.8; 204/299 R
[58] Field of Search ............ 204/299 R, 182.8, 183.3, 204/180.1, 301, 182.3

[56] References Cited

U.S. PATENT DOCUMENTS

| | | | |
|---|---|---|---|
| 3,901,782 | 8/1975 | Vadasz et al. | 204/182.8 |
| 4,321,119 | 3/1982 | Ambler | 204/183.3 |
| 4,351,709 | 9/1982 | Goetz | 204/183.3 |
| 4,578,169 | 3/1986 | Vicario et al. | 204/299 R |
| 4,661,225 | 4/1987 | Penniman et al. | 204/183.3 |
| 4,715,943 | 12/1987 | Place et al. | 204/182.8 |
| 4,801,366 | 1/1989 | Godfrey | 204/180.1 |
| 4,810,183 | 3/1989 | Place et al. | 204/299 R |
| 4,831,121 | 5/1989 | Montie et al. | 530/350 |

OTHER PUBLICATIONS

Electrophoretic Behavior of Mammalian-Type Cytochromes c Grant H. Barlow and E. Margoliash–The Journal of Biological Chemistry, vol. 241, No. 7, Issue of Apr. 10, 1966.

The Cataphoresis of Spherical, Solid Non-Conducting Particles in a Symmetrical Electrolyte by F. Booth–Proceedings of the Royal Society vol. A-203, Jun. 2, 1950.

Electrostatics: Its Application to Polar Molecules and Ionic Solutions by Edsall and Wyman–Biophysical Chemistry, vol. 1, 1958, New York: Academic Press, Inc., pp. 241-322.

The Cataphoresis of Suspended Particles–Part I. The Equation of Cataphoresis, by D. C. Henry, M. A., Proceedings of the Royal Society, vol. A-133, 1931.

(List continued on next page.)

Primary Examiner—John F. Niebling
Assistant Examiner—Arun S. Phasge
Attorney, Agent, or Firm—Robert Shaw

[57] ABSTRACT

A method of (and apparatus for) determining charge on protein or other macromolecule. The method involves providing two spaces, each containing buffer (e.g., water or saltwater), establishing a volume (a cuvette herein) between the two spaces, which volume contains the macromolecule in a solution that includes the buffer that establishes the pH of the solution (typically a pH of 0 to 12) and that further includes a gelling agent to inhibit convection. The macromolecule is confined to the volume (the cuvette); there is electrical continuity through the volume from the buffer in one space to the buffer in the other space; and there is flow of small molecules (e.g., of the buffer) from one space to the other through the volume. There is also external flow of buffer between the two spaces to maintain constancy of ionic contact therein as well as constancy and equality of liquid level, but no electric current flow between the spaces through or along the buffer in the external flow. A d-c electric field is established across the volume from one space to the other to establish an electrophoretic force on each macromolecule in the volume to cause each macromolecule to migrate therein, the diffusive force within the volume tending to counteract the electrophoretic force. The diffusive force is opposite to the electrophoretic force. After equilibrium between the two forces has occurred, the concentration distribution of macrómolecule is determined and the slope of the log of the concentration as a function of protein or curve fitting directly to the concentration direction is used to arrive at the charge on the macromolecule.

18 Claims, 4 Drawing Sheets

OTHER PUBLICATIONS

The Electric Potential Field Around Cytochrome c and the Effect of Ionic Strength on Reaction Rates of Horse Cytochrome c by W. H. Koppenol, C. A. J. Vroonland and R. Braams, Physics Laboratory, Dept. of Molecular Biophysics, University of Utrecht, Princetonplein 5, 3584CC 12/29/77.

The Kinetics of the Reduction of Cytochrome c by The Superoxide Anion Radical by W. H. Koppenol, K. J. H. Van Buuren, J. Butler and R. Braams, Physics Laboratory, Dept. of Molecular Biophysics, University of Utrecht, May 3, 1976.

Electrophoretic Mobility and Zeta Potential of Colloidal Particles by Peter McFadyen American Laboratory, Apr., 1987.

The Interpretation of Electrophorentic Mobilities by J. TH. G. Overbeek and P. H. Wiersema Mikon Bier, ed. 1967, Acad. Press, NY.

Introduction to Transport Processes: Diffusion by Van Holde, K. R. Physical Biochemistry (2nd ed.), New Jersey; Prentice Hall, 1985.

Calculation of the Electrophoretic Mobility of a Spherical Colloid Particle by P. H. Wiersema, A. L. Loeb and J. Th. G. Overbeek Journal of Colloid and Interface Science 22, 78–99, 1966.

The Settling of Small Particles in a Fluid by Max Mason and Warren Weaver Physical Review, vol. 23, 1924.

APPARATUS AND METHOD FOR MACROMOLECULAR CHARGE DETERMINATION

The present invention relates to systems that employ equilibrium electrophoresis to determine macromolecular charge and to equilibrium electrophoresis more broadly.

There accompanies herewith a copy of a paper submitted to Science entitled "Direct Determination of Macromolecular Charge by Equilibrium Electrophoresis," Laue et al., which is hereby incorporated by reference herein.

Attention is called to the following U.S. Pat. No. 3,719,580 (Roberts et al.), U.S. Pat. No. 3,720,593 (Juhos), U.S. Pat. No. 3,969,218 (Scott), U.S. Pat. NO. 4,164,464 (Allington et al.), and U.S. Pat. No. 4,323,439 (O'Farrell).

Attention is also called to Barlow, Grant H. and Margoliash, E. 1966, "Electrophoretic Behavior of Mammalian-type Cytochrome C," *Journal of Biological Chemistry*, 241, 1473–1477; Booth, F. 1950, "The cataphoresis of spherical, solid non-conducting particles in a symmetrical electrolyte," *Proc. Roy. Soc.*, A-203 514–433; Cooper, Terrance G. 1977, *The Tools of Biochemistry*, New York; John Wiley & Sons, Inc.; Edsall J. T. and Wyman, J. 1958, *Biophysical Chemistry*, vol. 1, New York; Academic Press, Inc., 241–322; Henry, D. C., 1931, "The cataphoresis of suspended particles. Part I-the equation of cataphoresis," *Proc. Roy. Soc.*, A-133, 106–137, Koppenol, W. H., Vroonland, C. A. J., and Braams R., 1978, "The Electric Potential Field Around Cyctochrome C and the Effect of Ionic Strength on Reaction Rates of Horse Cytochrome C," *Biochemica et Biophysica Acta*, 503, 499–508; Koppenol, W. H., Van Buren, K. S. H., Butler, J. and Braams, R., 1976, "The Kinetics of the Reduction of Cytochrome C by the Superoxide Anion Radical," *Biochimica et Biophysica Acta*, 499, 157–168; McFayden, Peter, April 1987, "Electrophoretic Mobility and Zeta Potential of Colloid Particles," *American Laboratory*, 64–75; Overbeek, J. and Wiersems, P. H., 1967, "The Interpretation of Electrophoretic Mobilities," *Electgrophoresis: Theory, Applications & Technique*, vol. 2, 1–49, New York: Academic Press; Van Holde, K. R., 1985, *Physical Biochemistry* (2d edition), 93–109, New Jersey; Prentice Hall; Wiersema, P. H., Loeb, A. L. and Overbeek, J. Th. G., 1966, "Calculation of the electrophoretic mobility of a spherical colloid particle," *Journal of Colloid and Interface Science*, 22, 78–99.

The term "equilibrium electrophoresis" is used herein to denote a situation in which a d-c or unidirectional electric field E is applied across a solution containing a macromolecule(s) (or macromolecular species) to create an electrophoretic force upon the macromolecule which is opposed by a diffusive force on the macromolecule. In this manner, equilibrium of the macromolecule(s) is achieved. The class of macromolecule of most interest and most discussed herein is protein; however, any soluble macromolecule (nucleic acid, carbohydrate or man-made polymer) may be examined by this method. Once this equilibrium is achieved, and as later discussed, the protein concentration along the direction of the electric field E is nonlinear and the logarithm of the gradient in such concentration, it has been found for present purposes, is proportional to the protein charge. Hence, according to the present teaching, the logarithm of the concentration gradient is used as a basis for determination of the protein charge (and other protein properties, e.g., aggregation properties).

A fundamental property of macromolecules in solution is their charge. Both biological and synthetic polymers can possess a net charge in solution. Many structural, kinetic and functional features of macromolecules result from their charges. Both the presence of charges and changes to them are important in determining the strength, specificity and rapidity of the interactions between molecules. Despite its importance, the net apparent charge is not a readily-accessible parameter experimentally. Extant methods (filtration, electrophoretic mobility measurements, estimation from composition, inference from structural determination) require a great deal of material, are conducted in nonphysiological buffers and can be in serious error due to the binding of solvent components by charged groups on the macromolecule.

Equilibrium electrophoresis opens to inquiry an entire area of physical chemistry of macromolecules that has suffered from a dearth of experimental methods. There are several immediate applications envisioned for this method. First, there is simply cataloging the apparent charge on important synthetic and biological polymers, including proteins, carbohydrates and nucleic acids, under a variety of conditions. More important will be the ability to measure changes in the apparent charge upon interaction of macroions with other molecules (solvent components, metal ions, or other macromolecules), including macromolecules of opposite-signed charge. Such measurements will allow direct quantitation of ionic interactions and their role in will allow direct quantitation of ionic interactions and their role in mediating structural and functional properties of macromolecules. Moreover, by correlating changes in charge with changes in structure, it will be possible to test and to extend various poly-electrolyte theories of considerable importance in understanding drug-DNA and protein-DNA interactions.

Accordingly, it is an objective of the present invention to provide a system for direct determination of charge on a macromolecule.

Another objective is to employ equilibrium electrophoresis for such purpose.

A further object is to provide a direct determination of charge on a macromolecule by a way that counteracts convection (i.e., by use of a gel at the interactive region).

A still further objective is to provide a system that uses buffer chambers but which is not hampered by ion disproportion between the chambers.

A still further objective is to provide a system that minimizes costs.

These and still further objectives are addressed hereinafter.

The foregoing objectives are achieved, generally, by apparatus (and method) for direct determination of charge on a macromolecule in solution, which apparatus includes two buffer chambers, which volume contains the macromolecule in a solution that includes the buffer that establishes and controls the pH of the solution and that further includes a gelling agent (to provide a high-porosity gel in the volume), the macromolecule being confined to the volume, there being electrical continuity between the buffer in the volume and the buffer in the two buffer chambers and flow of all small molecules between the two buffer chambers through said volume; a mechanism for providing external flow of buffer between the two buffer chambers as well as constancy and equality of liquid level in the two buffer chambers, there being no electric current between said chambers through said external flow of buffer; a mechanism for establishing an electric field in a direction across said volume to establish an electrophoretic force on each macromolecule to cause said each macromolecule to migrate within said volume, diffusive force in said volume tending to counteract said electrophoretic force, the electrophoretic force and the diffusive force being opposite to one another; a mechanism for determining the concentration distribution in the direction of the electric field, after an appropriate time lapse; and a mechanism for relating said concentration distribution to the charge. The system minimizes (or eliminates) the effect of convection in the volume.

The invention is hereinafter discussed with reference to the accompanying drawing in which.

Figure 1:
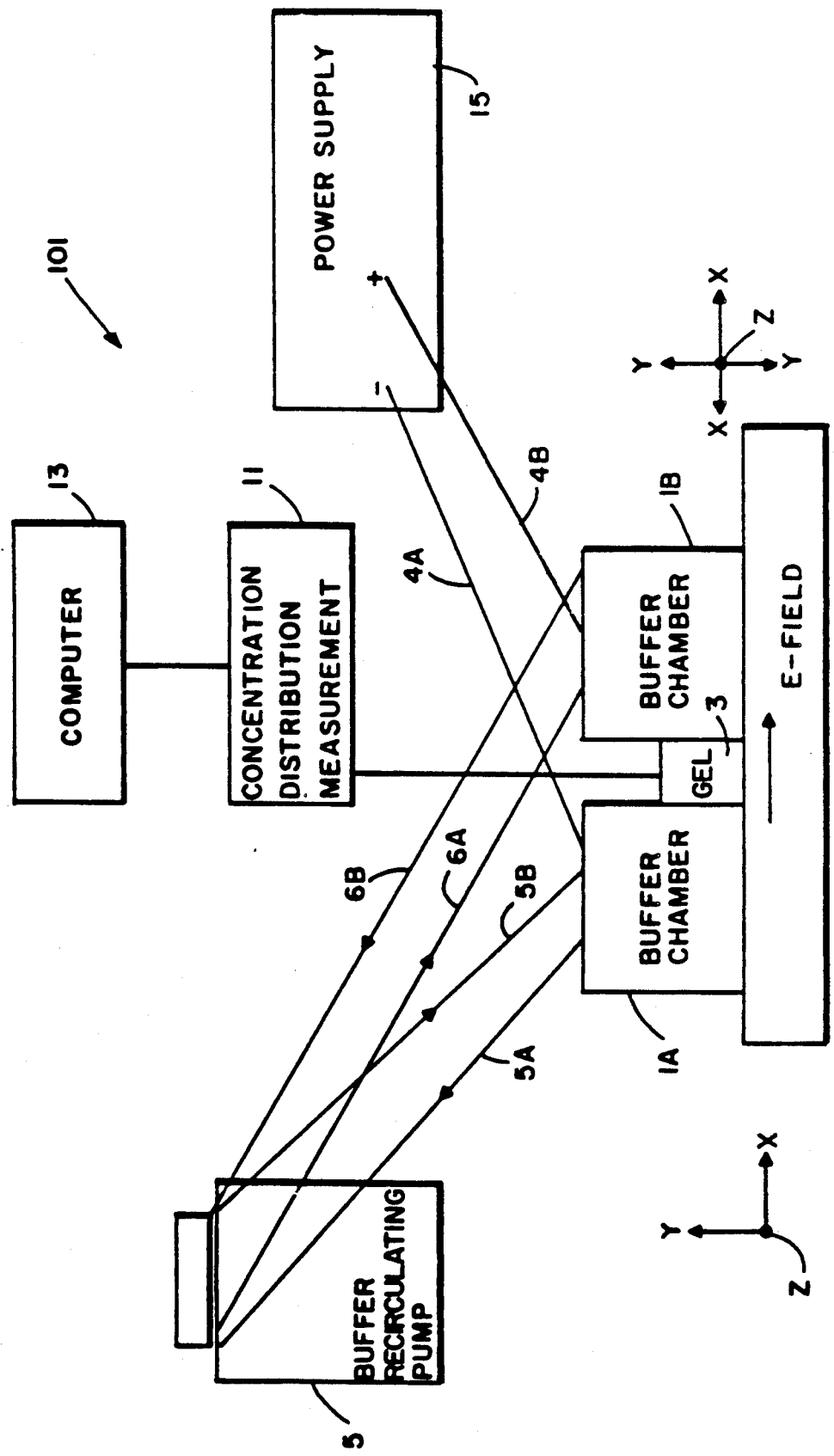
FIG. 1 is a diagrammatic representation of a system to achieve direct determination of charge on a macromolecule in solution by use of equilibrium electrophoresis.

Turning now to FIG. 1, the system labeled 101 provides direct determination of a charge on a macromolecule (e.g., protein) in solution. The system 101 includes two buffer chambers 1A and 1B within hollow rectilinear housings 20A and 20B in FIG. 2. A cuvette 3 establishes a volume between the two buffer chambers 1A and 1B, which volume contains the macromolecule in a solution that includes a buffer that establishes and controls the pH of the solution and that further includes a gelling agent that, among other things, inhibits convection in the solution, a most important issue. The shapes of the chambers 1A and 1B and the cuvette 3 are not important, but the physical dimensions of the cuvette 3 are. The shapes in the y-z plane in FIG. 1 are square. The dimensions of the cuvette in the y-z plane are one centimeter by one centimeter and its length in the x-direction is 0.3 centimeter, for reasons given below; and this is important. There is flow of fluid between the chambers 1A and 1B through the cuvette 3, as later explained, through dialysis membranes 2A and 2B (FIG. 2) at the ends (i.e., the portions of the cuvette 3 in contact with the chambers 1A and 1B, that is, an opening 31A in the housing 20A in FIG. 2 and a like opening in the housing 20B). The structures 20A, 20B, 3 and so forth, are nonconductive plastic (e.g., Delrin and the like). The macromolecule is confined to the volume, there being electrical continuity between the buffer in the volume (i.e., the cuvette 3) and the buffers labeled 7A and 7B in the two buffer chambers 1A and 1B in FIG. 2 (within the rectilinear housings 20A and 20B) and flow of all small molecules between the two buffer chambers 1A and 1B through the volume, that is, from chamber 1A to chamber 1B and vice versa through the cuvette 3. The cuvette 3 in the exploded portion of FIG. 2 includes a three-dimensional enclosed space 3A bordered by the semipermeable membranes 2A and 2B disposed at the liquid flow ends of the space 3A.

A buffer recirculating pump 5 provides external flow of buffer between the two buffer chambers 1A and 1B along tubes 5A, 5B, 6A and 6B to maintain constancy of buffer in the two buffer chambers as well as constancy and equality of liquid level in the two buffer chambers, there being no electric current between the chambers 1A and 1B through the external flow of buffer. The pump 5 is preferably a peristaltic pump. It pumps buffer in the tube 5A from the buffer chamber 1A to the tube 6A and thence to the chamber 1B; it pumps buffer in the tube 6B from the chamber 1B to the tube 5B and thence to the buffer chamber 1A. The buffer levels are designated 8A and 8B in FIG. 2. The end of the tube 5A is submerged in the buffer 7A (as is the end of the tube 6B in the buffer 7B), but the end of the tube 6A (and also 5B) is above the buffer level 8B to achieve electrical isolation with respect to the buffer in the respective tubes and the buffer in the respective chambers. The circles P plus arrows indicate pressure and directions of liquid flow.

Platinum wire electrodes 4A and 4B establish an electric field E in the x-direction across the cuvette volume to establish an electrophoretic force on each macromolecule to cause each macromolecule to migrate within the volume, diffusive force in the volume tending to counteract the electrophoretic force, the electrophoretic force and the diffusive force being opposite to one another. A mechanism 11, together with a computer 13, determines the concentration distribution in the direction of the electric field E (i.e., the x-direction) after an appropriate time lapse and relates that concentration distribution to the charge on the macromolecules.

As indicated, the hollow cuvette 3 establishes a volume which contains the macromolecule and a gelling agent, the cuvette being sealed at either end by the semipermeable membrane 2A and 2B that is porous to small molecules, including all solvent and buffer reagents, but impermeable to the macromolecules. (The membranes 2A and 2B used are dialysis tubing which is a treated cellulose-based material used for sausage casings.) There is external buffer exchange through the tubes 5A, 5B, 6A and 6B and the peristaltic pump 5, which takes buffer from one buffer (or first) chamber 1A, for example, and drips it into the other (or second) buffer chamber 1B and takes buffer from the other (or second) buffer chamber 1B and drips it into the first buffer 1A. As noted above, the tubes 5A . . . are arranged to maintain the level or height of the buffer constant and equal in the two chambers 1A and 1B, while providing electrical isolation between the chambers through the pump 5.

The concentration distribution measurement device or analyzer 11 can be a spectroscopic analyzer which provides instantaneous absorbance or fluorescence measurements at discrete locations along the electric field (i.e., in the x-direction). Likewise, refractrometric or conductivity measurements may be used to determine the concentration distribution instantaneously. Alternatively, this distribution can be assessed by using a chemical or physical assay, e.g., specific radioactive label, immediately subsequent to electrophoresis. The output of the analyzer 11 is connected to the computer 13 which is programmed in the manner herein indicated to provide the charge on the macromolecule in the gel solution in the cuvette 3.

Figure 3:
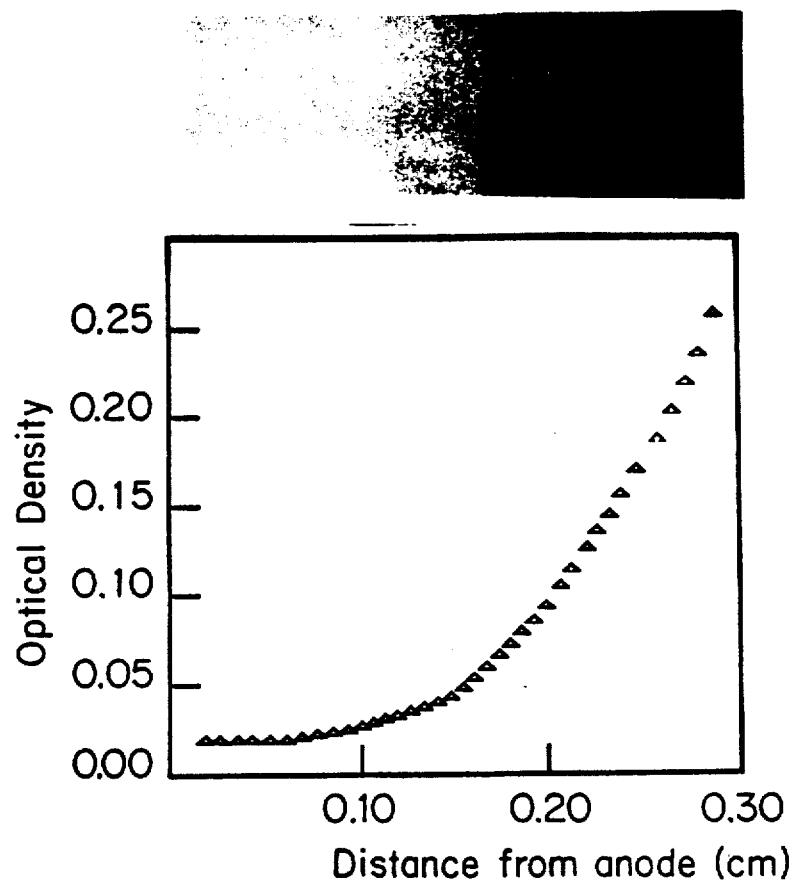
FIG. 3 is a graphic representation of concentration profiles of a sample of the macromolecule cytochrome C in the electric field E direction in the cuvette of the earlier figures, employing equilibrium electrophoresis.
Figure 4A:
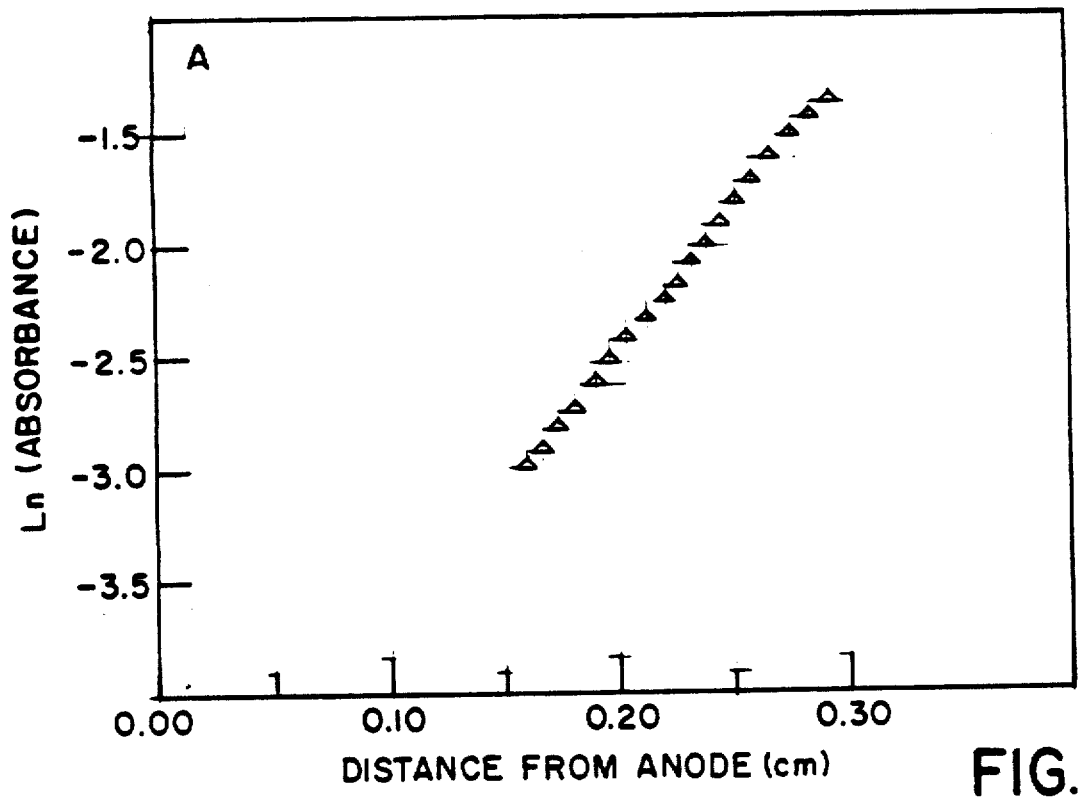
FIG. 4A is the natural logarithm of the optical density as a function of distance from the anode end of the cuvette, using the optical densities presented in FIG. 3 (equation 4 hereinafter predicts a straight line with slope directly proportional to the apparent charge)
Figure 4B:
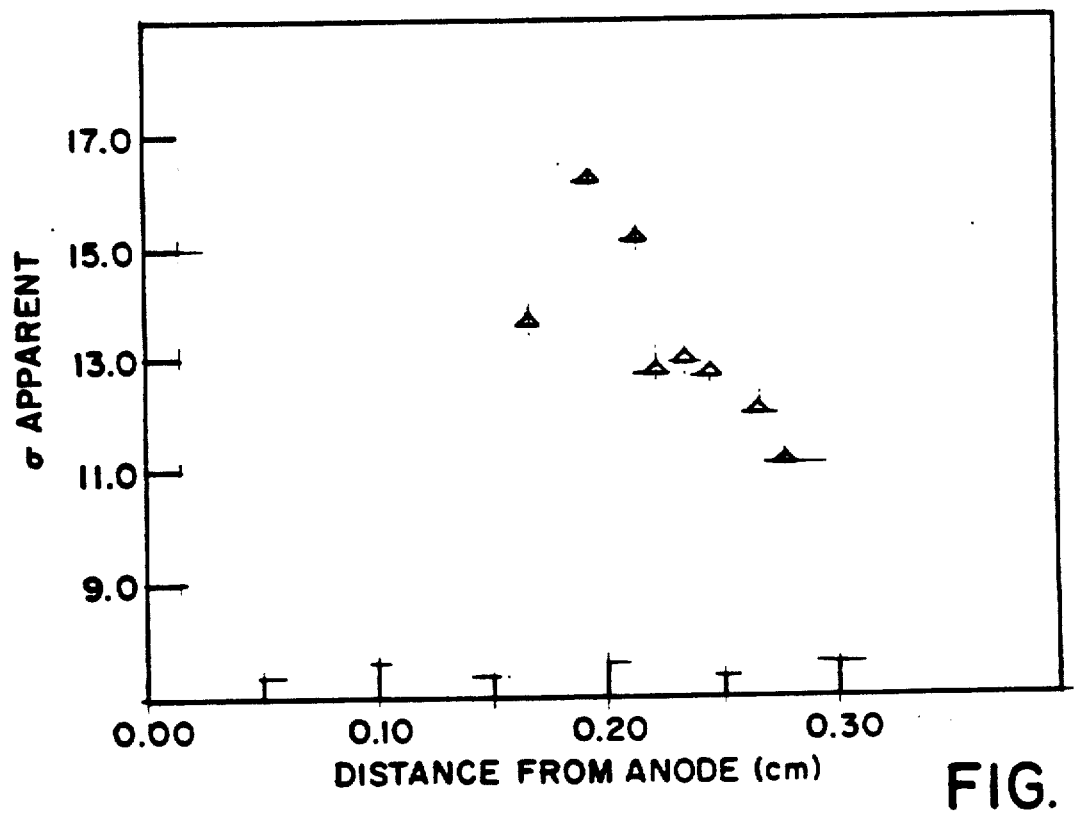
FIG. 4B is the local slope ($\sigma$-app) as a function of distance from the anode end of the cuvette.

Briefly, with reference to FIGS. 3, 4A and 4B, the concentration of the protein cytochrome C is shown graphically. A graph of a concentration profile for cytochrome C, along with a densitometric tracing of the transmittance is shown in FIG. 3. The transmittance at the anode (+) end is used as the zero-concentration, and the zero-corrected transmittance is converted to optical densities (-log transmittance) at each of about 30 positions along the x-axis (corresponding to 100 $\mu$M increments in the cell coordinates). A graph of the logarithm of the optical density as a function of x is presented in FIG. 4A; is the slope of the line in FIG. 4A and is linearly proportional to the apparent charge. Values of the slope can be calculated at each point x where there is sufficient optical density (>0.05 absorbance, typically), and this has been done in FIG. 4B using the method of Roark and Yphantis. Likewise, it is possible to fit the concentration profile (FIG. 3) directly to:

$$c(x) = \delta + \ln c_0 + \sigma \cdot [x - x_0] - 2 \cdot B \cdot [c(x) - \delta]$$

using nonlinear squares methods.

Figure 2:
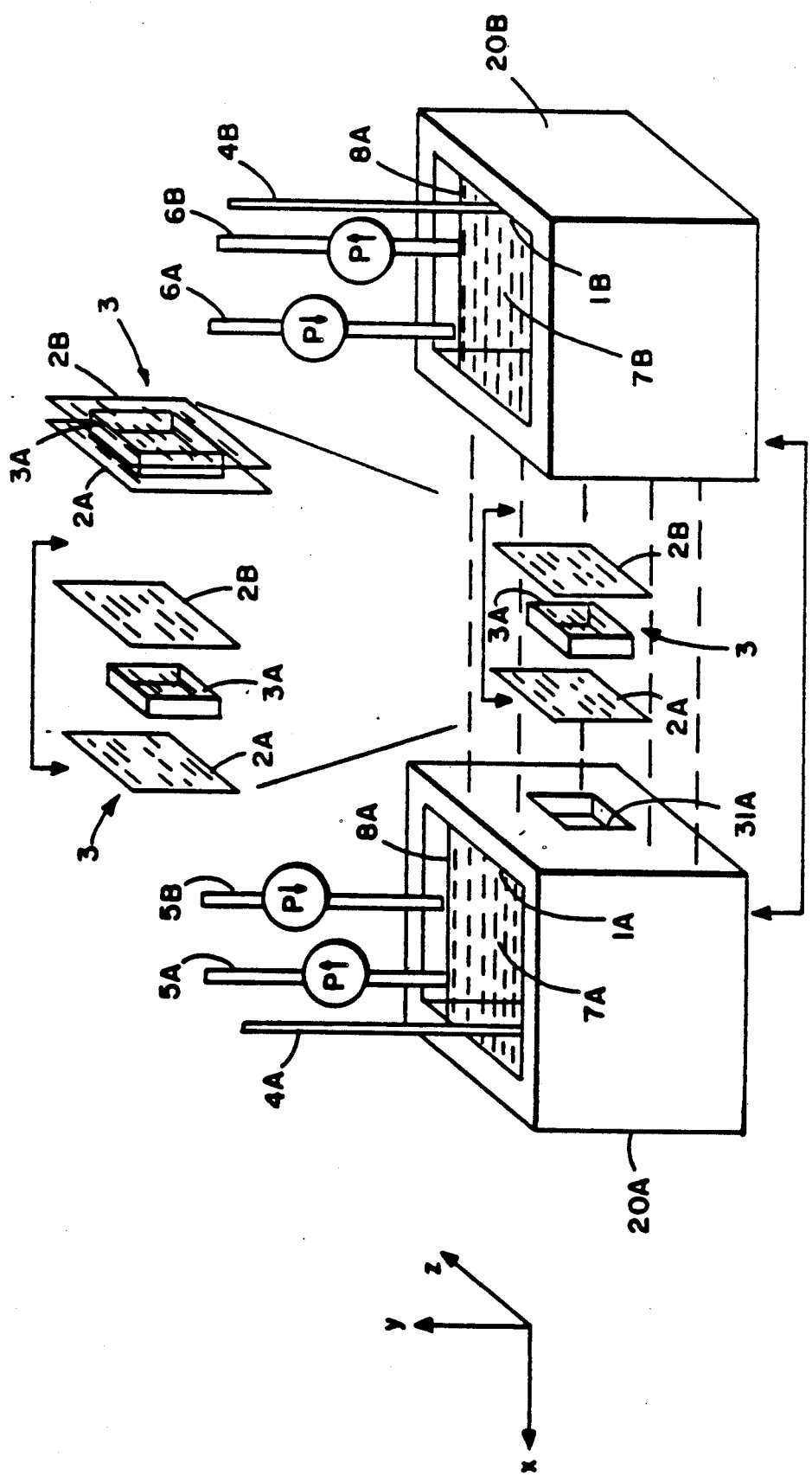
FIG. 2 is an exploded isometric view, partly diagrammatic in nature, and cutaway, of a portion of the system in FIG. 1, that includes a cuvette.

The essential apparatus in FIG. 2 are the buffer chambers 1A and 1B that contain the buffer 7A and 7B and the cuvette 3 that contains buffer as well as macromolecule. The buffer can move into and out of the cuvette 3 but the macromolecules cannot. An x-direction electric field E is established across the cuvette 3. Electrophoresis moves macromolecules in one direction. A diffusive force opposes the electrophoretic force, allowing the system to come to equilibrium, resulting in a protein (i.e., macromolecule) gradient that is proportional to the protein charge and that charge can be calculated in accordance with the equations herein. It is shown that the thickness (x-direction) of the cuvette 3 is important because equilibrium conditions take much, much longer as cuvette thickness increases. According to the present teaching the cuvette 3 is one-centimeter square (in the y-z plane in FIG. 2) and 0.3 centimeter thick, i.e., in the x-direction in FIG. 2.

Equilibrium electrophoresis, as noted, is a method of determining protein charge by opposing the electrophoretic force with a diffusive force, and allowing the system to come to equilibrium. The resulting protein concentration gradient is proportional to the protein charge. The theoretical considerations involved in the development of equilibrium electrophoresis are discussed herein, and an equation to calculate protein charge is derived. The design considerations in the building of the electrophoretic apparatus are also discussed.

Equilibrium electrophoresis is a relatively easy method of determining the absolute charge Q of a protein (or other large molecule). The force, due to electrophoresis, is approximately equal to QE, where E is the external x-directed electric field imposed on the macromolecule. Unfortunately the charge cannot be determined from this equation alone because the force is not a measurable parameter. If a force opposing the electrophoreses is applied, however, and the two forces are allowed to come to equilibrium, the force terms will cancel, allowing Q to be calculated.

The opposing force used is the force due to diffusion. The diffusive force normally present during any type of electrophoresis occurs both in and against the direction of migration, causing a protein initially migrating in a tight band to diffuse into a bell-shaped curve. The key to equilibrium electrophoresis is allowing diffusion only against the direction of migration. In this way, the diffusive force opposes the electrophoretic force. Then by measuring the concentration gradient necessary to provide the opposing force, a measure is available of the electrophoretic force.

Directing the diffusive force is accomplished by placing a barrier at the end of the running region (i.e., the cuvette 3) which allows the passage of solvent and small ions, but blocks protein migration. This is achieved in accordance with the present teaching by diffusive permeable walls 2A and 2B, FIG. 2, at the axially-spaced ends of the protein 3A of the cuvette 3. The protein will start to gather in a tight band against the plug (i.e., the wall 2B, for example), but the diffusive force will cause it to spread backward, away from the plug (i.e., the wall 2B). If electrophoretic conditions remain constant, the electrophoretic and diffusive forces will come to equilibrium. All of the parameters affecting the two forces, which will be described, are measurable, allowing the determination of Q.

The amount of time needed to reach equilibrium increases with the square of the length of the running region, the x-direction herein. The equilibrium time can be calculated either in terms of the electrophoretic velocity or in terms of the diffusion rate. In the forward direction, the protein migration rate is dictated by the electrophoretic velocity ($F = x/t$), where x is the distance of migration in the x-direction and t is the equilibrium time. In the reverse direction, the movement of protein is limited to the rate of diffusion. Under most conditions, diffusion is a much slower process than electrophoretic migration, so it is desirable to have the net protein movement in the forward direction. It is most practical to mix the protein with the gel before polymerization, so that the protein was initially distributed evenly through the gel. (Typically, the protein and the gel are mixed prior to gelation so that the protein starts out being distributed evenly throughout the cuvette 3.) In this case, the equilibrium time is still dictated primarily by the electrophoretic velocity, since the net protein movement will be in the forward (i.e., plus-x-direction) direction. It is important to remember that both electrophoretic migration and diffusion are x-direction and are occurring simultaneously, and the rates of both these processes are needed to determine how long it will take to reach equilibrium.

Even though the equilibrium time is primarily dictated by the electrophoretic velocity, the diffusion rate was used by the present inventors to calculate the equilibrium time for two reasons. First of all, the diffusion rate gives a more conservative estimate, so that no error will be made by assuming that equilibrium has occurred too soon. Second, the viscosity of the gel is needed in order to calculate the electrophoretic velocity of the diffusion (equation 4, below), and is difficult to quantify for a gel.

The equilibrium time due to diffusion (M. Mason and W. Weaver, *Phys. Review*, 23;412 (1924)) is governed by:

$$t = (x)^2/D, \tag{1}$$

where D is the diffusion coefficient, which for cytochrome equals $5 \times 10^{-7}$ cm$^2$/sec. Table 1, below, gives time versus the length in the x-direction of the running region. In order to reach equilibrium in a reasonable amount of time, a path length of 0.3 centimeter was decided upon for this research. The cuvette was cut to a length of 0.3 centimeter, and protein movement through either end was prevented by dialysis tubing with a size cutoff of 8000 daltons. The protein concentration gradient, $-d\ln C/dx$, which is used to calculate charge (equation 9, below), is unaffected by path length, although the actual concentration at any point may be increased by a shorter path length.

TABLE 1

|  | LENGTH OF RUNNING REGION | EQUILIBRIUM TIME |
| --- | --- | --- |
| Equilibrium time for different running region lengths (i.e., x-direction herein). Assuming $D = 5 \times 10^{-7}$ cm$^3$/sec. | 1.0 cm | 11.5 days |
|  | 0.5 cm | 3 days |
|  | 0.3 cm | 1 day |

An electric field E in FIG. 1 is established across the cuvette 3 in the x-direction (FIG. 1) which creates a flux J of macroions:

$$J_e(x) = [c(x)\Psi/f_e] \cdot E \qquad (2)$$

where $J_e(x)$ is the flux in g/cm$^2$-sec at a point x along the x-axis in the cuvette and in the direction of the field (i.e., from cathode to anode); c is the mass concentration of the macroion, $\Psi$ is its apparent net charge in coulombs and $f_e$ is its translational frictional coefficient as it would be measured in the electric field. Diffusion is used as the counter flux:

$$J_D(x) = -D \, dc(x)/dx \qquad (3)$$

where $J_D(x)$ is the flux in g/cm$^2$-sec at point x, c(x) is the concentration and dc(x)/dx is the concentration gradient at that point, and D is the diffusion coefficient in cm$^2$/sec. When power is applied, the macroions move in response by the field. However, since they are confined to the semipermeable membranes 2A and 2B, their concentration increases at the membrane surface proximal to the electrode possessing the opposite-signed charge. Since a concentration gradient in the macroion develops, a flux due to diffusion also develops, but in the opposite direction to that due to electrophoresis. Eventually an equilibrium is reached at each point x such that the magnitudes of the fluxes due to electrophoresis and due to diffusion are exactly equal. Equating the magnitudes of the two fluxes (Eq. 2 and 3), and rearranging:

$$d[\ln c(x)]/d\chi = -E\Psi/(f_e D) \qquad (4)$$

Equation 4 is analogous to that obtained for sedimentation equilibrium. Analysis of the results from equilibrium electrophoresis for nonassociating systems, including those that are heterogeneous, will be identical to that for sedimentation. Further evaluation of Eq. 4 is possible using the Einstein-Sutherland equation for D:

$$D = [k_B T/f_t] \cdot [1 + \partial(\ln \gamma)/\partial(\ln c)] \qquad (5)$$

where $k_B$ is Boltzmann's constant ($1.3807 \times 10^{-23}$ J/°K), T is the absolute temperature, $f_t$ is the translational friction coefficient and $\gamma$ is the activity coefficient. In the limit $c \rightarrow 0$, $D = D_o = kT/f_t$.

The electric field may be calculated from measurable parameters:

$$E = i(\chi A) \qquad (6)$$

where i is the current in amperes, $\chi$ is the specific conductivity in mho$^-$·cm$^{-1}$, and A is the cross-sectional area of the cuvette in the y-z plane (FIG. 2). It should be noted that an experimenter has three experimentally accessible options (i, $\chi$, A) for manipulating E to a useful range. The resulting equation is:

$$d[\ln c(x)]/d\chi = [i/\chi A] \cdot [f_t f_e] \cdot [\Psi/k_B T]/[1 + \partial(\ln \gamma)/\partial(\ln c(x)]  \qquad (7)$$

It will be noted that as E approaches zero, $f_e$ must approach $f_t$, and their ratio becomes one. This approximation should valid for the present method since E is small (typically less than 0.2 volt/cm). Moreover, the assumption that $f_t/f_e = 1$ is testable since, if this is so, values of $\Psi$ determined at different E $(=i/\chi A)$ should be constant. With this assumption, equation 7 becomes:

$$d[\ln c(\chi)]/dx = -[i/\chi A] \cdot [\Psi/k_B T]/[1 + \partial(\ln \gamma)/\partial(\ln c(x)] \qquad (8)$$

and in the limit $c \rightarrow 0$;

$$d[\ln c(x)]/d\chi = -[i/\chi A] \cdot [\Psi/k_B T] \qquad (9)$$

For the purposes of nonlinear least squares fitting, equation 8 is rewritten:

$$c(x) = c_o \exp[\sigma \cdot [x - x_o] - 2B(c(x) - c_o) \qquad (10)$$

where c(x) is the concentration at a point x along the axis of the electric field $c_o$ is the concentration at $x_o$, an arbitrary reference position in the cuvette, $\sigma = [i/\chi A] \cdot [\Psi/k_B T]$, $x_o$ is the reference position, and B is the second virial coefficient. The ideal case is modeled by holding B=O.

Reduced cytochrome C was used for experimentation discussed herein, and has an estimated charge of +8 at pH 7.5.

The experiment included electrode trays and the platform which holds them were machined out of Delrin (a plastic), as before noted. To avoid the presence of metal, which may affect the electrical circuit, all of the fasteners were likewise made of plastic. The running chamber or cuvette 3 was a polystyrene cuvette with the bottom removed. The cuvette was held in place between the two electrode trays by a washer seal; the seal was tightened by a screw which pressed one of the electrode trays, which was movable, and the cuvette, against the other tray, which was stationary.

The protein was run in a loose matrix of polyacrylamide (3.0 percent). The pore size of 3.0 percent acrylamide is about 30 nm, which is large enough to allow cytochrome C (1.7 nm) to pass through relatively uninhibited throughout the cuvette 3. A loose matrix is desirable to decrease the friction so that equilibrium will be reached more quickly and it minimizes the effects of the gel on the specific conductivity.

Further modifications of the invention herein disclosed will occur to persons skilled in the art and all such modifications are deemed to be within the scope of the invention as defined by the appended claims.

What is claimed is:

1. A method of direct determination of charge on a macromolecule in solution, that comprises:

providing two buffer chambers;

establishing a volume between the two buffer chambers, which volume contains and confines the macromolecule in a solution that includes the buffer that establishes and controls the proton concentration or pH of the solution and that further includes a gelling agent, the macromolecule being confined to the volume, there being electrical continuity between the buffer in the volume and the buffer in the two buffer chambers and flow of all small molecules between the two buffer chambers through said volume;

providing external flow of buffer between the two buffer chambers to maintain constant ionic concentrations of buffer in the two buffer chambers as well as constancy and equality of liquid level in the two buffer chambers, there being no electric current between said chambers through said external flow of buffer;

establishing an electric field in a direction across said volume to establish an electrophoretic force on each macromolecule to cause said each macromolecule to migrate within said volume, diffusive force in said volume tending to counteract said electrophoretic force, the electrophoretic force and the diffusive force being opposite to one another;

after an appropriate time lapse determining the concentration distribution in the direction of the electric field; and relating said concentration distribution to the charge.

2. A method according to claim 1 in which the electric field is a d-c or unidirectional field, and in which the macromolecule is a protein.

3. Apparatus direct determination of charge on a macromolecule in solution, that comprises:

two buffer chambers;

means establishing a volume between the two buffer chambers, which volume contains and confines the macromolecule in a solution that includes the buffer that establishes and controls the pH of the solution and that further includes a gelling agent, the macromolecule being confined to the volume, there being electrical continuity between the buffer in the volume and the buffer in the two buffer chambers and flow of all small molecules between the two buffer chambers through said volume;

means providing external flow of buffer between the two buffer chambers to maintain constancy of buffer in the two buffer chambers as well as constancy and equality of liquid level in the two buffer chambers, there being no electric current between said chambers through said external flow of buffer;

means establishing an electric field in a direction field across said volume to establish an electrophoretic force on each macromolecule to cause said each macromolecule to migrate within said volume, diffusive force in said volume tending to counteract said electrophoretic force, the electrophoretic force and the diffusive force being opposite to one another;

means determining the concentration distribution in the direction of the electric field, after an appropriate time lapse; and means for relating said concentration distribution to the charge.

4. Apparatus according to claim 3 in which the electric field is a d-c or unidirectional field in which the macromolecule is a protein, in which the means for determining the concentration distribution is a spectroscopic analyzer and in which the means for relating is a computer connected to receive, as input, an output from the spectroscopic analyzer, which computer is operable to relate the concentration distribution to charge.

5. Apparatus according to claim 3 in which the means establishing a volume comprises a cuvette containing the gelling buffer and macromolecule, said cuvette being sealed at either end with a semipermeable membrane that is porous to small molecules including all solvent and buffer reagents but impermeable to said macromolecules.

6. Apparatus according to claim 5 in which means for providing external buffer exchange is a peristaltic pump which takes buffer from one buffer chamber and drips it into the other buffer chamber and takes buffer from the said other buffer chamber and drips it into said one buffer chamber, there being tubing between the pump and the two buffer chambers to carry the buffer, said tubing being arranged to maintain the level or height of buffer constant and equal in the two chambers, while providing electrical isolation between the chambers through the pump.

7. Apparatus according to claim 3 in which the electric field is established and maintained by a constant current power source.

8. Apparatus according to claim 3 in which the means for determining the concentration distribution is a spectroscopic analyzer which provides instantaneous absorbance or fluorescence measurements at discrete locations along the electric field.

9. Apparatus according to claim 3 in which the volume contains structures suitable for conductance measurement at each of a number of discrete locations along the electric field, which conductance measurements serve as a basis for said determination of charge.

10. Apparatus according to claim 3 in which the refractive index or refractive increment of the solution in said volume is sensed at each of a number of locations along the electric field, to provide data for said determination of charge.

11. Apparatus according to claim 3 in which, subsequent to the test run, thin sections or slices of the material in the volume are assayed chemically, physically (including use of radio isotopes) or biologically to determine the concentration distribution.

12. A method of direct determination of electric charge on a macromolecule in solution, that comprises:

providing two separated spaces, each containing a buffer;

establishing an enclosed space or volume between the two separated spaces, which enclosed space or volume contains the macromolecule in a solution that includes the buffer that establishes and controls the pH of the solution and that further includes an agent or mechanism to inhibit convection within the solution, the macromolecule being confined to and by the enclosed space or volume in all directions of flow, there being electrical continuity between the buffer in the enclosed space or volume and the two separated spaces and flow of all small molecules between the two separated spaces through the enclosed space or volume;

establishing an electric field across the enclosed space or volume in the direction between said two separated spaces to establish an electrophoretic force on each said macromolecule to cause the each said macromolecule to migrate within the enclosed space or volume, the diffusive force within said enclosed space or volume tending to counteract the electrophoretic force which is opposite to the diffusive force to effect a concentration distribution in the direction of the electric field;

after a time lapse determining the concentration distribution; and relating said concentration distribution to said charge.

13. Apparatus for direct determination of electric charge on a charged macromolecule in solution, that comprises:

means providing a plurality of separated spaces, each of the spaces containing a buffer;

means establishing a volume between the two separated spaces, which volume contains the macromolecules in a solution that includes the buffer and that further includes an agent or mechanism to inhibit convection within the solution, said means establishing being adapted to confine the macromolecule to the volume, there being electrical continuity through said volume between the buffer in said separated spaces;

means establishing an electric field across the volume in the direction therein between the separated spaces to establish an electrophoretic force on the macromolecules within the volume to cause said macromolecule to migrate within the volume in the direction of the electrophoretic force, diffusive force within the volume tending to counteract the electrophoretic force to achieve a concentration distribution within said volume; and means to relate said concentration distribution to said charge.

14. Apparatus according to claim 13 in which the means providing the plurality of separated spaces comprises two spatially-separated buffer chambers and in which said volume is disposed therebetween such that there is electric charge flow from one of the two spatially-separated buffer chambers to the other of the two spatially-separated buffer chambers through said volume.

15. A method of direct determination of electric charge on a macromolecule in solution, that comprises:

providing two separated spaces, each containing a buffer;

establishing a volume between the two separated spaces, which volume contains and confines the macromolecule in a solution that includes the buffer that establishes and controls the pH of the solution and containing and confining the macromolecule to the volume, there being electrical continuity between the buffer in the volume and in the two separated spaces and flow of all small molecules between the two separated spaces;

establishing an electric field in a direction across the volume in the direction between said two separated spaces to establish an electrophoretic force on each said macromolecule to cause the each said macromolecule to migrate within the volume, the diffusive force within said volume tending to counteract the electrophoretic force which is opposite to the diffusive force to effect a concentration distribution in the direction of the electric field;

inhibiting convection within the solution;

after a time lapse determining the concentration distribution; and relating said concentration distribution to said charge.

16. Apparatus for direct determination of electric charge on a charged macromolecule in solution, that comprises:

means providing a plurality of spaced spaces, each of the spaces containing a buffer;

means establishing a volume between the two separated spaces, which volume contains and confines the macromolecule in a solution that includes the buffer, said means establishing being adapted to contain and confine the macromolecule to the volume, there being electrical continuity through said volume between the buffer in said separated spaces;

means establishing an electric field across the volume in the direction therein between the separated spaces to establish an electrophoretic force on the macromolecule within the volume to cause said macromolecule to migrate within the volume in the direction of the electrophoretic force, diffusive force within the volume tending to counteract the electrophoretic force to achieve a concentration distribution within said volume;

means to inhibit convection of the solution within said volume; and means to relate said concentration distribution to said charge.

17. Apparatus for direct determination of electric charge on a charged macromolecule in solution, that comprises: means providing a plurality of separated spaces, each of the spaces containing a buffer; means establishing a volume between the two separated spaces, which volume contains and confines the macromolecule in a solution that includes the buffer, said means establishing being adapted to contain and confine the macromolecule to the volume, there being electrical continuity through said volume between the buffer in said separated spaces; means establishing an electric field across the volume in the direction therein between the separated spaces to establish an electrophoretic force on the macromolecule within the volume to cause said macromolecule to migrate within the volume in the direction of the electrophoretic force, diffusive force within the volume tending to counteract the electrophoretic force to achieve a concentration distribution within said volume; and means to relate said concentration distribution to said charge, wherein said volume is adapted to receive a mixture containing macromolecules possessing opposite-signed charge, which apparatus is operable simultaneously to measure charge on each opposite-signed charge particle of said mixture.

18. Apparatus for direct determination of electric charge on a charged macromolecule in solution, that comprises: means providing a plurality of separated spaces, each of the spaces containing a buffer; means establishing a volume between the two separated spaces, which volume contains and confines the macromolecule in a solution that includes the buffer, said means establishing being adapted to contain and confine the macromolecule to the volume, there being electrical continuity through said volume between the buffer in said separated spaces; means establishing an electric field across the volume in the direction therein between the separated spaces to establish an electrophoretic force on the macromolecule within the volume to cause said macromolecule to migrate within the volume in the direction of the electrophoretic force, diffusive force within the volume in the direction of the electrophoretic force, diffusive force within the volume tending to counteract the electrophoretic force to achieve a concentration distribution within said volume; and means to relate said concentration distribution to said charge, wherein said volume is removable with said concentration distribution intact therein for subsequent physical, chemical or biological assay.

* * * * *

UNITED STATES PATENT AND TRADEMARK OFFICE
CERTIFICATE OF CORRECTION

PATENT NO. : 4,994,161

DATED : February 19, 1991

INVENTOR(S) : Thomas M. Laue; David A. Yphantis; Andrea L. Hazard

It is certified that error appears in the above-identified patent and that said Letters Patent is hereby corrected as shown below:

The sheets of drawings consisting of Figs. 3, 4A and 4B, should be added as shown on the attached pages.

Drawing Sheet 1, change "Sheet 1 of 2" to: --Sheet 1 of 4--.

Drawing sheet 2, change "Sheet 2 of 2" to: --Sheet 2 of 4--.

Signed and Sealed this

Twenty-first Day of April, 1992

Attest:

HARRY F. MANBECK, JR.

Attesting Officer

Commissioner of Patents and Trademarks